(12) United States Patent
Thorne et al.

(10) Patent No.: US 7,326,324 B2
(45) Date of Patent: Feb. 5, 2008

(54) PURIFICATION AND USE OF GELLAN IN ELECTROPHORESIS GELS

(75) Inventors: Linda Thorne, Fallbrook, CA (US); Richard W Armentrout, Decatur, IL (US)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 467 days.

(21) Appl. No.: 10/717,976

(22) Filed: Nov. 20, 2003

(65) Prior Publication Data

US 2004/0168920 A1   Sep. 2, 2004

Related U.S. Application Data

(60) Provisional application No. 60/427,988, filed on Nov. 20, 2002.

(51) Int. Cl.
*C07K 1/26* (2006.01)

(52) U.S. Cl. .................... 204/469; 536/25.6; 536/23.1; 536/123; 435/178

(58) Field of Classification Search ................ 204/469; 536/25.6, 23.1, 123; 435/178
See application file for complete search history.

(56) References Cited

U.S. PATENT DOCUMENTS

| | | | |
|---|---|---|---|
| 4,326,052 A | 4/1982 | Kang et al. | 536/1 |
| 4,326,053 A | 4/1982 | Kang et al. | 536/1 |
| 4,377,636 A | 3/1983 | Kang et al. | 435/101 |
| 4,385,123 A | 5/1983 | Kang et al. | 435/253 |
| 5,143,646 A | 9/1992 | Nochumson et al. | 252/315.3 |
| 5,185,466 A | 2/1993 | Kozulic et al. | 564/208 |
| 5,202,007 A | 4/1993 | Kozulic | 204/182.8 |
| 5,259,943 A | 11/1993 | Kozulic et al. | 204/299 R |
| 5,278,270 A | 1/1994 | Kozulic et al. | 526/304 |
| 5,319,046 A | 6/1994 | Kozulic et al. | 526/304 |
| 5,342,773 A | 8/1994 | Thorne et al. | 435/200 |
| 5,371,208 A | 12/1994 | Kozulic | 536/102 |
| 5,438,092 A | 8/1995 | Kozulic et al. | 524/555 |
| 5,541,255 A | 7/1996 | Kozulic | 525/54.3 |
| 5,767,196 A | 6/1998 | Kozulic | 525/54.3 |
| 5,840,877 A | 11/1998 | Kozulic | 536/25.4 |
| 6,203,680 B1 | 3/2001 | Cole | 204/469 |

FOREIGN PATENT DOCUMENTS

EP   0 012 552 B1   12/1982

OTHER PUBLICATIONS

"Gellan (PS-60)" in Carbohydrate Chemistry, Kennedy, J.F. (ed.), Oxford University Press, Oxford, 1987, Section 14.4.4, p. 630.*
Cole, K. et al., "Modification of the Electrokinetic Properties of Reversible Electrophoresis Gels for the Separation and Preparation of DNA," *Applied Biochemistry and Biotechnology* 82(1): 57-76, Oct. 1999.
Doner, L. W. and Douds, D. D., "Purification of Commercial Gellan to Monovalent Cation Salts Results in Acute Modification of Solution and Gel-forming Properties," *Carbohydrate Research* 273: 225-233, 1995.
Jasson, P-E and Lindberg, B., "Structural Studies of Gellan Gum, and Extracellular Polysaccharide Elaborated by *Pseudomonas elodea*," *Carbohydrate Research 124*: 135-139, 1983.
O'Neil, M.A. et al., "Structure of the Acidic Extracellular Gelling Polysaccharide Produced by *Pseudomonas elodea*," *Carbohydrate Research 124*(1): 123-133, Dec. 10, 1983.
Sanderson, G.R., "Gellan Gum," in *Food Gels*, P. Harris (ed.) Elsevier Applied Science, New York 1990, Chapter 6, pp. 201-232.
Sanderson, G.R. and Clark, R.C., "Gellan Gum, a New Gelling Polysaccharide," in *Progress in Food and Nutrition Science*, vol. 7, Phillips, G.O. et al. (eds.), Pergamon Press, Oxford, 1984, pp. 201-210.
The Polysaccharides, vol. 2, Aspinall, G.O. (ed.), Academic Press, New York, 1983, p. 479.

* cited by examiner

*Primary Examiner*—Leon B. Lankford, Jr.
*Assistant Examiner*—Susan E. Fernandez
(74) *Attorney, Agent, or Firm*—Seed IP Law Group PLLC

(57) ABSTRACT

Gellan can be purified from nucleic acid contamination by combining the contaminated gellan with DNase under conditions that allow the DNase to degrade the nucleic acid contaminant. The purified gellan is useful in gel electrophoresis. A buffer which allows cystamine to be used as a reversible cross-linker does not have to be recirculated during the course of a normal gel run.

40 Claims, No Drawings

PURIFICATION AND USE OF GELLAN IN ELECTROPHORESIS GELS

CROSS-REFERENCE TO RELATED APPLICATION

This application claims the benefit of U.S. Provisional Patent Application No. 60/427,988 filed Nov. 20, 2002, where this provisional application is incorporated herein by reference in its entirety.

BACKGROUND OF THE INVENTION

1. Field of the Invention

The present invention is related to gellan purification, electrophoresis gel compositions containing purified gellan, and methods related thereto.

2. Description of the Related Art

Gel electrophoresis is currently employed for the separation of charged biological macromolecules such as proteins and nucleic acids. In gel electrophoresis, a mixture of charged species is resolved into its components owing to different mobilities of these species in a gel medium under an imposed electric field. The mobilities depend in large part on the characteristics of the charged species, including their net surface charge, which is affected by molecular size and shape.

Many types of gel material are suitable for use as the electrophoresis medium. The gel is often the determining factor in achieving a successful resolution of biological macromolecules, and accordingly the development of suitable gel materials has been the subject of intense research. Many gels are commercially available, and are typically composed of natural or synthetic polymers. Agarose is the most widely used natural material and polyacrylamide gels are the most common synthetic matrix.

In recent years, reversible gels have become commercially available and are increasingly popular for the purpose of preparative applications. In preparative applications, sections of the gel medium containing target biomolecules are reverted to the solution phase and the biomolecules therein are recovered by various means. For example, U.S. Pat. No. 5,143,646 describes the use of polysaccharide gel blends for stacking electrophoresis systems, wherein the gels are described as being "thermoreversible" and "pH reversible". In these particular reversible gels, the structure of the gel matrix is converted to a liquid form when the gel is subjected to heat or pH variation. Concerns have been raised, however, with regard to the conditions for reverting the "thermoreversible" or "pH reversible" gels to solutions. Problematically, the high temperature or specific pH (lower than 3 or higher than 9) needed for liquefying the gels can denature or otherwise alter the biomolecules contained in the gel matrix.

U.S. Pat. No. 6,203,680 discloses that gellan gum may be used as a reversible electrophoresis gel medium. Gellan-based gels have the advantage of being reversible under relatively mild conditions, and therefore address the concern about having the liquefication conditions harm the biomolecules. Gellan gum can be liquefied under mild conditions because it can form a cross-linked gel in the presence of either divalent cations or diamines. In the case where divalent cations are used as the cross-linking agent, liquefaction of the gel may be achieved by adding a sequestering agent specific for the divalent cation. When diamine is used as the cross-linking agent, the pH of the gel is maintained at a value such that the amino groups of the diamine are protonated. The gellan gel reverts to a liquid solution when the gel pH is adjusted so that the amino groups of the cross-linking agent are no longer protonated. This can be achieved under relatively mild pH conditions. Gellan-based electrophoresis gel can also be formed in the presence of cross-linked diamines that contain disulfide bonds. Gel formed in this way can be returned to solution using a reducing agent to break the disulfide bonds. A typical disulfide-containing cross-linker is cysteine dimethyl ester, also referred to as cystamine.

Gellan gum can be purified via a series of deionization and precipitation steps as described in Doner et al., "Purification of Commercial Gellan to Monovalent Cation Salts Results in Acute Modification of Solution and Gel-Forming Properties," Carbohydrate Research (1995), 273, 225-233. This purification procedure is time consuming and costly. Therefore, there exists a need in the art for gellan purified in an alternative and inexpensive way so it becomes economical to use gellan as a replacement for agarose.

BRIEF SUMMARY OF THE INVENTION

The present invention provides a method by which gellan, including commercial preparations of gellan, can be modified to render them particularly useful in electrophoresis gels. For instance, the present invention provides a method for purifying gellan where the method includes: (a) combining DNase and gellan, the gellan being contaminated with nucleic acid, thereby providing a mixture; and (b) maintaining the mixture of step (a) under conditions where the DNase degrades at least some of the nucleic acid, thereby providing purified gellan. Optionally, a size-separation property modifying polymer such as poly(ethylene oxide) may be added to the gellan or the purified gellan. In various optional embodiments, the gellan is contaminated with more than 100 ppm, or more than 10 ppm of nucleic acid, based on weight parts of gellan. The method of the present invention can reduce the nucleic acid contamination by 50% or more, e.g., to a level of less than 1 ppm nucleic acid based on weight parts of gellan. A DNase activating agent may be added to speed to rate of nucleic acid degradation, where sodium azide is a preferred DNase activating agent. Typically, the mixture of step (a) is maintained at about 30-45° C. for at least about 1 hour. Within less than about 24 hours, the nucleic acid has been essentially completely degraded. After the gellan has been treated to degrade the nucleic acid, the DNA may, optionally, be deactivated. For example, the treated mixture may be taken to a DNase inactivating temperature in excess of about 50° C.

The present invention thus provides gellan having very low levels of nucleic acid contamination. For example, the gellan may be in mixture with either no nucleic acid, or nucleic acid at a concentration of less than 10 ppm, or less than 5 ppm, or less than 1 ppm nucleic acid, where the ppm values are based on weight parts of gellan. These purified gellans are particularly useful in preparing an electrophoresis medium. For instance, the purified gellan may be in combination with a buffer composition suitable for maintaining said composition at a pH of 5-9. A buffer composition with imidazole or a salt thereof and boric acid or a salt thereof is a preferred buffer composition, where the buffer may additionally contain EDTA or a salt thereof. To form a suitable gel for electrophoresis, the purified gellan is in combination with a cross-linking agent. A preferred cross-linking agent is cystamine.

The present invention provides a superior method for treating gellan. Alternative methods require that the preparations be diluted, run over columns and then reprecipitated in an organic solvent. This is labor intensive and expensive. Our easy method allows gellan preparations to be used as an economical electrophoresis matrix that can be used as an agarose alternative.

The present invention also provides kits useful in gel electrophoresis. In one aspect, the invention provides a kit that contains: (a) a matrix composition comprising gellan and nucleic acid at a concentration of less than 10 ppm based on the weight of the gellan; (b) buffer; and (c) cross linking agent such as cystamine. The kit may optionally contain a size-separation property modifying polymer such as poly (ethylene oxide). The gel matrix may optionally include boric acid or a salt thereof and/or imidazole or a salt thereof, and may be at a pH between about 6.5 and 8.5. The kit may also contain a separate container of buffer, e.g., imidazole and boric acid buffer. The matrix may optionally include a DNA stain.

The invention also provides a method of performing electrophoresis. The method includes forming an electrophoresis medium by combining ingredients that include: (a) a matrix composition that includes gellan, nucleic acid at a concentration of less than 10 ppm based on the weight of the gellan, and size-separation property modifying polymer; (b) buffer; and (c) cross linking agent. The electrophoresis medium is normally placed in an electrophoresis chamber and an electric field is applied across the medium.

The invention also provides an electrophoresis apparatus. The apparatus includes: (a) a cross linked matrix formed by combining gellan in combination with nucleic acid at a concentration of less than 10 ppm (or less than 5 ppm, or less than 1 ppm) based on the weight of the gellan (preferably prepared according to the methods of the present invention), cross linking agent, buffer, and size-separation property modifying polymer; and (b) an apparatus for exposing said cross linked matrix to an electric field.

The present invention also provides a method for recovering a biological material. This method includes: (a) adding a mixture comprising a biological material to a cross linked electrophoresis medium, the medium being formed by a method comprising combining a cross linking agent and gellan contaminated with less than 10 ppm (or less than 5 ppm, or less than 1 ppm) nucleic acid based on the weight of the gellan (preferably prepared according to the methods of the present invention); (b) exposing the medium to an electric field to separate in said medium said biological material from other components in the mixture; (c) removing a zone of the medium containing the biological material from the medium; (d) exposing the removed zone to an agent that reverses the cross linking of the medium, to provide liquefied electrophoresis medium; and (e) separating the biological material from the liquefied electrophoresis medium, thereby recovering the biological material. The cross-linking agent may optionally be a divalent metal cation, where the agent that reverses the cross linking is a chelating agent. Alternatively, the cross-linking agent may be a diamine and the agent that reverses the cross linking is pH modifying agent. Alternatively, the cross-linking agent has a disulfide bond, and the agent that reverses the cross-linking is a reducing agent that can reduce a disulfide bond to two thiol groups.

The present invention also provides a composition that includes water, imidazole or a salt thereof, and boric acid or a salt thereof, where this composition is particularly useful as a buffer, particularly when the composition has a pH between 5 and 9, e.g., between 6 and 8. To achieve this pH, the imidazole or salt thereof typically has a concentration between 10 and 100 mM, e.g., 20-60 mM, or about 44 mM, while the boric acid or salt thereof typically has a concentration between 50 and 500 mM, e.g., 100-300 mM, or about 200 mM. EDTA or a salt thereof may optionally be included in this composition The buffering composition of the present invention can be used with cystamine as a cross-linking agent for gellan. Cystamine is a reversible cross-linker that allows gellan preparations to form a gel. The imidazole/boric acid buffering system of the present invention maintains a pH range wherein the cystamine is kept in a protonated form and thus functions as a cross-linking agent. During gel electrophoresis, it is not necessary to recirculate the imidazole/boric acid buffering system of the present invention in order to retain its efficacy as a buffer, which is a great advantage of the present invention because buffer recirculation is very inconvenient for researchers.

These and other aspects of the present invention are described in greater detail below.

DETAILED DESCRIPTION OF THE INVENTION

For purposes of describing the present invention, the following terms have the indicated meaning.

Definitions

The term "biomolecule" refers to nucleic acids such as DNA and RNA, oligonucleotides, peptides, proteins, and other biological materials that can be separated using electrophoresis techniques, including mixtures thereof.

The terms "cross-linking agent" and "cross-linker" refer to an additive which induces or promotes the association of the gellan molecules in solution, resulting in gel formation. Controlled changes to the chemical or physical structure of the cross-linking agent may optionally revert the gel into liquid solution. Examples of cross-linking agents are divalent cations and diamines, including diamines containing disulfide bonds.

The term "cystamine" refers to cysteine dimethyl ester. Cystamine contains two amino groups and one disulfide bond, and may be used as a cross-linker for the gellan gel formation.

The terms "degrade" and "degradation" refer to depolymerization of an oligonucleotide or polynucleotide. Degradation of an oligonucleotide or polynucleotide will generally occur through enzymatic hydrolysis of internucleotide phosphodiester bonds to release short oligonucleotides and/or mononucleotides.

The term "divalent metal cation" refers to divalent group IIA cations such as $Ca^{2+}$, $Mg^{2+}$, $Sr^{2+}$, $Ba^{2+}$, etc. and to divalent transition metal cations such as $Zn^{2+}$, $Mn^{2+}$, $Cu^{2+}$, etc.

The term "diamine" refers to organic compounds having two amine groups such as ethylene diamine, and 1,3 diamino-2-hydroxypropane (DAHP), etc. The term "polyamine" refers to organic compounds having two or more amine groups. A suitable polyamine is a star-shaped dendrite in which there are amino groups at the end of the arms of the star. Typically, the amine groups of a diamine or polyamine are separated from each other by a hydrocarbon or hydrocarbon derivative chain.

The term "disulfide" refers to the —S—S— bond. An example of a compound containing a disulfide bond is cystamine.

The term "DNase" refers to an enzyme that degrades DNA.

The term "DNase activating agent" refers to any material that may be added to the gellan during the gellan purification process of the present invention, wherein the agent enhances the speed and/or completeness of the degradation of the nucleic acid contaminant in gellan as compared to the same process in the absence of such an agent. Agents that activate DNase activity are known in the art. Sodium azide is a DNase activating agent.

The terms "electroosmosis" and "electroosmotic flow" refer to the movement of a charged substance through a charged matrix or other barrier by way of an electric field-induced convective flow.

The term "electrophoretic mobility" refers to the steady-state velocity induced per unit field strength for a selected biomolecule during electrophoresis. Electrophoretic mobility can be measured in terms of the time required for a biomolecule to travel a specific distance in the gel, or in terms of distance traveled by a molecular species from a reference point along the length of the gel during a selected time.

The term "ethylene oxide" refers to a monomeric unit having the formula —$CH_2CH_2$—O—.

The terms "gellan gum" and "gellan" refer to a family of related carbohydrate polymers produced by Sphinogomonas bacteria (previously identified as *Pseudomonas*), and includes native gellan gum, clarified gellan gum, deacetylated gellan gum, gellan gum that is both clarified and deacetylated, chemically modified gellan, and gellan gum produced by genetically engineered bacteria.

Native gellan is described in Kennedy, J. F., *Carbohydrate Chemistry*, page 630 (1988) Clarendon Press, Oxford, as an extracellular anionic polysaccharide produced by the bacterium *Pseudomonas eloclea* (ATCC 31461). According to Kennedy, gellan from this source is a partially O-acetylated linear polymer of D-glucose, L-rhamanose, and D-glucuronic acid, which has the basic repeating unit, excluding acetyl groups, of ? 3)-β-D-Glcp-(1? ∝)-β-D-GlcpA-(1? 4) -β-D-Glcp-(1? 4)-a-L-Rhap-(1?, which may also be written as GlcA 1-4 Glu 1-4 Rha 1-3 Glu, where "GlcA" represents glucuronic acid, "Glu" represents glucose and "Rha" represents rhamanose. According to Kennedy, in gellan, 33% of the monosaccharide residues are oxidized monosaccharide residues, and cellobiuronic residues constitute 66 wt % of the monosaccharide residues in the polysaccharide.

Gellan is also described in Aspingall (The Polysaccharides, vol. 2, Academic Press, 1983, page 479) as obtained from *Pseudomonas elodea* and contains a glucose:rhamanose ratio of 2:1. Aspingall states that gellan could be obtained from Kelco, Division of Merck & Co., Inc. as PS-60. PS-60 is available in three grades, namely: (a) "native", which contains 11% uronic acid, 3% acetylated uronic acid, 10% protein, 7% ash, and a 2:1 ratio of glucose to rhamanose; (b) "deacetylated", which contains 13% uronic acid, no acetylated uronic acid, 17% protein and 8% ash, with a 2:1 ratio of glucose to rhamanose; and (c) "deacetylated and clarified", which contains 22% uronic acid, no acetylated uronic acid, 2% protein, 9.5% ash, and a 2:1 ratio of glucose to rhamanose. "Clarified" gellan is described below.

Gellan is also described in the following references: U.S. Pat. Nos. 4,326,052; 4,326,053; 4,377,636; and 4,385,123. Other descriptions of gellan may be found in, for example, Jansson et al., *Carbohydr. Res.* 124, 135, 1983; and Sanderson et al. *Progress in Food and Nutrition Science*, vol. 7, (eds. G. O. Phillips, et al., p. 201, Pergamon Press, Oxford, 1984).

Certain gellans are currently commercially available. For example, GELRITE™ is produced from a naturally occurring polysaccharide after deacetylation and "clarification", where clarification refers to a process wherein the polysaccharide is fully or partially removed from the bacterial debris. GELRITE™ is available from a variety of sources including, for example, Sigma Chemical Co., St. Louis, Mo. Essentially the same material is also available from Sigma Chemical under the trade name PHYTAGAR™.

The terms "nucleic acid" and "oligonucleotide" and "polynucleotide" are used interchangeably herein to refer to a polymeric form of nucleotides. In one aspect, the nucleic acid is at least five bases in length, i.e., it contains at least five nucleotides. The nucleotides of the invention can be deoxyribonucleotides, ribonucleotides, or modified forms of either nucleotide.

The term "polypeptide" refers to a molecule including at least two linked amino acid residues and derivatives thereof.

The term "poly(ethylene oxide)" refers to a molecule containing a plurality of ethylene oxide units. While a poly(ethylene oxide) necessarily contains a plurality of ethylene oxide groups, the poly(ethylene oxide) referred to herein may, but not necessarily does, contain groups other than ethylene oxide groups. For example, the poly(ethylene oxide) may contain terminal groups (i.e., groups at the ends of the molecule) other than hydroxyl groups, e.g., hydrocarbon groups. As another example, the poly(ethylene oxide) may include propylene oxide groups, i.e., groups of the formula —$CH(CH_3)CH_2$—O—. The poly(ethylene oxide) is preferably water-soluble. In one aspect of the invention, ethylene oxide is the only repeating unit in the poly(ethylene oxide), while in another aspect, at least 90 molar percent of the repeating units in the poly(ethylene oxide) are ethylene oxide. The number average molecular weight of the poly(ethylene oxide) useful in gel electrophoresis is typically 100,000 to 5,000,000.

The term "purification" is defined as the DNase treatment of gellan that decreases, but does not necessarily eliminate, background fluorescence in the presence of DNA stains (e.g., ethidium bromide, SYBER Green, Gel Star, etc.) where this background fluorescence is caused by interaction between high molecular weight DNA and the DNA stain. A "purified" gellan of the present invention has been subjected to DNase treatment such that there is less background fluorescence in the presence of DNA stain relative to the amount of background fluorescence observed with the corresponding non-purified gellan, i.e., the gellan that has not yet gone through the treatment of the present invention.

The term "reducing agent" refers to any agent that can affect the reduction of a disulfide bond, thereby breaking the bond without causing a chemical change on any other substituent on the cross-linking agent. An example of a reducing agent is dithiothreitol (DTT).

The term "reversibility" is used to refer to the ability of gellan gels to be returned to a liquid state.

The term "size-separation property modifying polymer" refers to polymers that can be incorporated into the gellan-containing gel of the present invention to alter the size-separation properties of the electrophoresis medium formed from the gellan. Examples of size-separation property modifying polymers include hydroxyethyl cellulose, dextran, ficoll, poly(alkyleneoxide) including polyethylene oxide, pullulan, starch, and linear polyacrylamide.

The terms "zone" and "band" refer to a portion of an electrophoresis medium or gel that contains substantially one biological material. Depending on the purity desired in a particular application of the present invention, there may be some degree of other biomolecules in a given zone in addition to the biological material that is to be recovered using the method of the present invention.

Description

The present invention is directed to a novel purified gellan and a treatment method that provides the purified gellan. Additionally, the invention is directed to gellan compositions that are particularly useful as electrophoresis gels. The invention also provides apparatus and methods for performing high-resolution separation and recovery of nucleic acids, proteins and other biomolecules. Furthermore, the present invention provides a buffer system that is particularly useful in combination with gellan.

As discussed above, gellan gum is a linear carbohydrate polymer produced by bacterial fermentation. See, e.g., in U.S. Pat. Nos. 4,326,052; 4,377,636; 4,385,123 and European Patent No. 0 012 552, the entire disclosure and contents of which are hereby incorporated by reference. The carbohydrate polymer consists of repeating tetrasaccharide units composed of two glucose sugars, a rhamnose and a glucuronic acid. This structure is described more completely in O'Neil et al., "Structure of the Acidic Polysaccharide by *Pseudomonas* elodato" in *Carbohydrate Research* (1983), 124, 123-133 and Jansson et al, "Structural Studies of Gellan Gum, an Extracellular Polysaccharide Elaborated by *Pseudomonas* elodato" in *Carbohydrate Research* (1983), 124, 135-139. The gellan gum produced by typical fermentation has both O-acetyl and O-L-glyceryl 3-linked to glucose units. The acetyl groups can be removed during processing and the resulting materials are called low acyl gellan gums as described in Sanderson, Food Gels, P. Harris (ed.) Elsevier Applied Science, (New York: 1990), 202-232. Commercially available low acyl gellan gums are available under the tradenames KELCOGEL™, GELRITE™ and PHYTAGEL™ gelllan.

Gellan has a number of unique properties that make it a desirable medium for electrophoresis and a potential replacement for agarose as one of the most widely used electrophoresis gels. In the presence of a cross-linking agent, gellan gum forms strong gels in a range of polymer concentrations and buffer compositions. Accordingly, these gels are suitable for high-resolution electrophoresis and the subsequent recovery of the separated biomolecules. Gellan-based gel has the additional advantage of being "reversible" in that the gel can be returned to a liquid state under relatively mild conditions, typically by sequestering or chemically altering the cross-linking agent. Furthermore, gellan forms gel at substantially lower concentration than agarose. Electrophoresis gels having gellan contents of as low as 0.03 wt % may be constructed, however the most useful range of gellan gels for DNA electrophoresis is between 0.1 wt % and 0.5 wt %. In contrast, agarose gel formation typically requires the presence of 0.8-3 wt % agarose. Particularly when gel electrophoresis is followed by recovery of the separated biomolecules, it is advantageous to use a minimum amount of gellant (e.g., agarose, gellan) so that there is less gellant that needs to be separated from the recovered matrix.

A common step in electrophoretic separations is to add a fluorescent dye to the gel matrix. The dye will preferentially bind to the biomolecule in the matrix. Thus, after the biomolecules have been resolved, the entire gel can be placed under a source of ultraviolet (UV) radiation and a prominent signal appears at positions in the gel where biomolecule is located. The present inventors have discovered that when commercial grade gellan is used as the gel matrix in electrophoresis separation, the expected bands due to fluorescent dye localization near biomolecule are not observed as expected. Thus, this routinely used approach to locating biomolecule-containing zones in electrophoretic separations was found to be unsatisfactory when commercial grade gellan was used as the gel matrix. The present inventors have not only identified the cause of this unexpected problem, but have also discovered a solution as described herein.

The present inventors have discovered that gel cast from commercially available gellan gives off strong background fluorescence across the gel, where this background fluorescence partially, and sometimes largely, obscures the fluorescence emitting from zones of separated nucleic acid molecules. The present invention provides a method for purifying gellan based on the finding that commercial or other untreated gellan contains nucleic acid contaminant associated with the gellan. Though the nucleic acid contaminant does not affect formation of the gel or the separation of the biomolecules during electrophoresis, it interferes with the visualization of the biomolecules that have been resolved, particularly when the biomolecules are nucleic acids.

Thus, the present invention provides a method for purifying gellan comprising the steps of (a) combining gellan and a DNase, where the gellan is contaminated with nucleic acid, thereby providing a mixture; and (b) maintaining the mixture of step (a) under conditions where the DNase degrades at least some of the nucleic acid, thereby providing purified gellan. In various optional embodiments, the starting gellan is contaminated with 1-1000 ppm nucleic acid based on weight parts of polysaccharide, or 10-1000 ppm nucleic acid, 1-500 ppm nucleic acid, or 10-500 ppm nucleic acid, or 1-100 ppm nucleic acid, or 10-100 ppm nucleic acid, or 1-50 ppm nucleic acid, or 10-50 ppm nucleic acid. In certain embodiments, the starting gellan is contaminated with at least 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 150, 200, 250, 300, 400, 450, 500, 600, 700, 800, 900, or 1000 ppm nucleic acid based on weight parts of polysaccharide.

In contrast, commercially available gellan has about 20-30 ppm nucleic acid. For example, KELCOGEL® gellan has about 24 ppm nucleic acid, KELCOGEL F® gellan has about 20 ppm nucleic acid, and GELRITE® gellan has about 28 ppm, where these values are obtained by measuring the absorbance at 260 nm, i.e., the $OD_{260}$ value, as measured on a spectrophotometer using a 0.5 wt % aqueous gellan solution, and calculating nucleic acid concentration using the Warburg-Christian calculation method. The Warburg-Christian method is described in O. Warburg and W. Christian (1942) Biochem. Z. 310:384-424, and entails measurement of absorbance ratios at 260 nm and 230 nm, and again at 260 nm and 280 nm. Background correction is made using absorbance values at 320 nm, taking into consideration the factors outlined by Warburg & Christian.

Gellan is commercially available in a solid form. In one aspect, solid gellan is combined with water to create a suspension of the gellan in water. This suspension is conveniently created by combining about ca. 2 or less grams of solid gellan with ca. 100 grams of water so as to provide an aqueous suspension having about 2 wt % or less gellan. In other words, 2 parts gellan are combined with 100 parts water. When the concentration of gellan in the suspension is greater than about 2 wt %, then the suspension tends to be lumpy and non-uniform due to non-uniform wetting of the particulate gellan, where this consistency is less amenable to action by DNase. The water that is used to prepare the gellan suspension is preferably of low ionic strength, such as deionized or distilled water.

In order to expedite formation of the suspension, the gellan-water mixture is preferably maintained at slightly elevated temperature, e.g., 35-40° C., for approximately 2 hours with agitation. When higher temperature is used, the gellan tends to dissolve in the water rather than form a suspension in the water. While a solution of gellan may also be combined with DNase according to the present invention, it is observed that DNase tends to degrade nucleic acid more slowly in a gellan solution than in a gellan suspension. A gellan solution is also somewhat disadvantageous in that it tends to gel without the addition of added cross-linking agents, and thus becomes very viscous. In a gellan suspension, a gellan concentration of less than 2 wt %, e.g., 0.5 wt %, is generally preferred in order to create a mixture that has workable properties. While temperatures of less than 37° C. may be used to form the gellan suspension, it is observed that a uniform suspension tends to form more slowly as the temperature is reduced much below about 37° C. While agitation for about 2 hours is typically adequate to create a uniform-appearing aqueous gellan suspension, either longer or shorter times may be used. Longer agitation times tend to allow more of the gellan to dissolve in the water, with a concomitant increase in viscosity. Shorter agitation times do not always allow all of the gellan particles to wet and become suspended in the water. In one aspect, the mixture of gellan and water is maintained at 30-45° C. for at least 0.5 hour, more typically at least 1 hour, and still more typically at least 2 hours.

Maintaining the water and gellan mixture at about 37° C. is also convenient because after the suspension has formed, it is at a temperature that is conducive for DNase activity. As defined herein, DNase is an enzyme that is capable of digesting or degrading nucleic acid, i.e., polynucleotide. Nucleases can be endo or exo. A commercially available and preferred DNase is known as DNase 1, which is an endonuclease. The DNase can simply be added to the aqueous gellan suspension to begin the nucleic acid degradation. At temperatures higher than about 60° C., the DNase denatures and becomes inactive. At temperatures lower than about 30° C., the DNA degrading activity of the DNase slows considerably. Accordingly, it is preferred but not necessary that the gellan suspension or solution be maintained at about 37° C. during the time when the DNase is expected to degrade the nucleic acid.

The DNase may be added at any convenience concentration. In general, as more DNase is added, the rate of nucleic acid degradation increases, but the cost to prepare the purified gellan also increases due to the expense of the DNase. A suitable concentration of DNase can be readily determined by using skill available to one of ordinary skill in the art. A method to monitor the nucleic acid degradation process is described later herein. A DNase concentration of about 1-10 units/mL in a 2 wt % gellan suspension is observed to provide a good rate for nucleic acid degradation, i.e., most or all of the nucleic acid degrades within about 6 hours, and the cost for the DNase is not excessive. In this description, a unit is defined by the Kunitz assay, where one unit produces an increase in absorbance of $1\times10^3$/min under assay conditions.

In addition to the DNase, in one aspect of the invention a DNase activating agent is added to the water/gellan mixture to enhance the speed of Dnase-induced degradation of the nucleic acid contaminant. DNase activating agents such as divalent cations are known in the art, however these also cross-link gellan. The present inventors unexpectedly found that sodium azide also appears to activate DNase 1. Without intending to be bound by their theory, the present inventors believe this is because their modification of the gellan polymer gives DNase better access to the contaminating DNA. The sodium azide also served to prevent bacterial growth during the incubation period. Sodium azide is inactivated by the heat treatment used to inactivate the Dnase as discussed below. As one means for adding the DNase activating agent to the water/gellan mixture, it is convenient to prepare a solution of the DNase activating agent, and then add some of that solution to the water/gellan/DNase mixture. For instance, sodium azide may be prepared as a 5 wt % solution in water, and then a sufficient amount of this solution is added to the water/gellan/DNase mixture to provide a sodium azide concentration of about 1-5 mM, e.g., 3 mM.

The extent of the degradation process can be monitored by taking small samples of the mixture and staining them with ethidium bromide followed by observing the fluorescence of the sample. An ethidium bromide concentration of about 0.5 mM is suitable. The purification is at least partially complete when there is reduced background fluorescence observed in the sample. Another approach is to monitor the optical density of a sample of gellan suspension, where the absorbance at 260 nm is directly proportional to the concentration of nucleic acid in the suspension. For this procedure it is necessary to precipitate the sample with isopropanol or ethanol, then dry and resuspend the sample. For example, a 0.25 wt % gellan suspension in water, prior to addition of DNase, may have an $OD_{260}$ of about 0.2, which corresponds to a nucleic acid concentration of about 0.3 μg DNA/mL solution, or 24 ppm nucleic acid based on weight parts of gellan. Over the course of about 2 hours at 37° C. in the presence of 4 units DNase/mL solution, the $OD_{260}$ drops to a level that corresponds to a nucleic acid concentration of less than 0.05 μg DNA/mL solution, or in other words, less than 1 ppm nucleic acid based on weight parts of gellan. This procedure is conveniently used for determining times and concentrations needed to optimize the nucleic acid degradation reaction. It is not needed to prepare gellan for use in DNA electrophoresis.

In general, any reduction in nucleic acid contamination of gellan is desirable because this reduction means that there is less background noise created when the gellan is used in an electrophoresis gel, and a nucleic acid intercalating agent is used to visualize the resolved nucleic acid. In one aspect of the invention, at least 50% of the nucleic acid initially present in contact with the starting gellan is degraded by the DNase, as determined by the $A_{260}$ method described above. In other aspects, the present invention provides a method whereby the nucleic acid contamination is reduced to less than 60%, or less than 70%, or less than 80%, or less than 90% of the starting nucleic acid contamination, preferably to below 1 ppm nucleic acid based on the weight parts of gellan. Thus, in various aspects of the invention, purified gellan compositions are provided that comprise water and gellan, wherein (a) the composition contains either no nucleic acid or nucleic acid at a concentration of less than 10 ppm based on weight parts of gellan, or (b) the composition contains either no nucleic acid or nucleic acid at a concentration of less than 5 ppm, or (c) the composition contains either no nucleic acid or nucleic acid at a concentration of less than 1 ppm.

Upon completion of the nucleic acid degradation, the DNase that is in mixture with the purified gellan may be deactivated by heating the DNase to a deactivating temperature. This thermal deactivation may be accomplished by, e.g., heating the aqueous DNase/gellan mixture to a temperature in excess of about 60° C. for a time in excess of about 1 minute. After this thermal deactivation step, the purified gellan may be cooled and store at ca. room temperature.

The thermal deactivation step may optionally be omitted, and the product suspension provided to the end-user with active DNase. It is not necessary to heat the purified gellan for the sole purpose of deactivating the DNase because in the normal course of gel preparation, the gellan solution will be heated to above 75° C. This heating step is performed in order to, for example, completely dissolve the gellan in the water and to provide a sufficiently low viscosity solution that it can be easily poured into the mold that forms the electrophoresis gel. During this heating process, any active DNase present in the gellan suspension will typically be destroyed.

In one aspect of the invention, the purified gellan is used to form a gel for electrophoretic separation of biomolecules. In the preparation of such a gel, there is no need to recover the purified gellan from the suspension in order to use the gellan to form an electrophoresis medium. This is particularly true when the concentration of the gellan in the purified gellan is greater than the concentration of gellan needed for the gel. It is a simple matter to treat concentrated suspensions of gellan and to dilute the purified gellan to a concentration suitable for forming a gel. In general, a typical gellan concentration for casting electrophoresis gel is approximately 0.175 wt %. Accordingly, as a matter of convenience, the concentration of gellan in the purified gellan prepared according to the present invention should be greater than approximately 0.1 wt %. Thus, preparing an initial gellan suspension having a concentration of about 1.5-2 grams gellan/100 g water, i.e., about 1.5-2 wt % is a preferred aspect of the present invention.

As mentioned above, the purified gellan gums of the present invention may be formed into electrophoresis gels. These gels may be formed according to techniques that are well known and commonly used in the art when, for example, agarose is the gel matrix. In general, gel slabs for gel electrophoresis can be prepared from aqueous gellan suspensions having gellan concentrations ranging from about 0.03 to 2 grams/100 g aqueous suspension, where a concentration range of 0.1 to 0.5 grams/100 g aqueous suspension is preferred to impart a relatively high mechanical strength to the gel, without using more gellan than is necessary. One of the advantages to using gellan in gel electrophoresis is that a suitable gel slab can be prepared using less gellan than would be required if the slab were prepared from agarose. Thus, a concentrated gellan suspension may be diluted to about 0.3 g gellan/100 g water using, for example, additional water or buffer. The solution is then heated to ensure that all gellan particles dissolve completely.

In preparing a gel for gel electrophoresis, the gellan gum may be cross-linked to afford a gel having relatively high mechanical strength. High mechanical strength is generally desirable in a gel being used in gel electrophoresis. The cross-linking of gellan may be accomplished by techniques known in the art, e.g., using either a divalent metal cation or a diamine, as two examples. When the cross-linking agent is a divalent metal cation, any of a variety of divalent metal cations can be used, such as group IIA metal cations, such as $Ca^{2+}$, $Mg^{2+}$, $Sr^{2+}$, $Ba^{2+}$, etc., or transition metal cations such as $Zn^{2+}$, $Mn^{2+}$, $Cu^{2+}$, etc. The divalent metal cations are generally added to the gellan gum solution in the form of a metal salt. Typically, the gellan gum is mixed with the divalent metal cation cross-linking agent at a temperature above about 60° C., and the resulting solution is allowed to cool to form the gel. This temperature will typically be sufficient to inactivate any active DNase still present in the gellan suspension. The divalent metal cation is preferably also added to the electrophoresis buffer solution that will be used in conjunction with the electrophoresis medium, preferably at a concentration of about 0.1 to 10 mmol/L.

In the case of divalent metal cation cross-linked gels, after electrophoresis, the separated bands can be detected using a variety of means including specific stains or direct scanning of the gel. The bands (zones) containing the resolved solutes (biomolecules) can be recovered by a variety of means including cutting the band out of the electrophoresis gel, and combining the isolated band with a chelating compound specific for the divalent cation used as the cross-linking agent. The chelating compound may be in solution form or attached to a solid substrate, such as an ion exchange resin.

Electrophoresis gels of the present invention employing diamine cross-linking agents can be formed in a similar manner as that followed when divalent cation is used as the cross-linker. Thus, the diamine may be mixed with the gellan gum at a temperature above about 60° C. Any buffer used in conjunction with the diamine cross-linked gels of the present invention should maintain the gel at a pH below the pK's of the amino groups of the diamine so that the amino groups are protonated when they are intended to function as cross-linking groups. The pH needs to be selected in view of the selection of the diamine cross-linking agent. For example, the methyl esters (blocked carboxyl groups) of lysine, arginine, and histidine, all form stable gels at pH below 7, preferably 5 to 7.

In the case of diamine cross-linked gels, after electrophoresis, the separated bands can be detected using a variety of means including specific stains or direct scanning of the gel. The bands containing the resolved solutes (biomolecules) can be separated from the bulk matrix by mechanical means, e.g., a knife or spatula, and then the biomolecule present in the isolated band can be recovered by a variety of means including adding a base to the gel either in solution form or attached to a solid substrate, such as an ion exchange resin. Once the pH of the band is increased to the point where the amino groups of the diamine cross-linking agent are no longer largely protonated, the gel reverts to a liquid.

A preferred diamine for the present invention is cysteine dimethyl ester, also referred to as cystamine. Cystamine is formed from two cysteine methyl esters linked at the side chains through a disulfide bond, where each cysteine methyl ester has a blocked (methylated) carboxyl group and a free amino group. As a diamine, cystamine can be added to a gellan solution as a cross-linking agent to form a strong and stable electrophoresis gel. The gel can be readily converted back to solution in the presence of a reducing agent that breaks the disulfide linkage between the two cysteine methyl esters. An example of a suitable disulfide reducing agent is DTT (dithiothreitol).

Although the above-described gellan electrophoresis gel uses a diamine (cystine dimethyl ester) to form the gel, thiol groups can also be introduced into the gellan gum polymer by covalent bonds. As mentioned above, gellan gum has a charged carboxyl group that can bind to cations. The carboxyl groups can also be used as an attachment point to make various gellan gum derivatives. The carboxyl group is a reactive site that can be covalently attached to thiol or other functional groups. The carboxyl group reacts with amine-containing compounds optionally in the presence of carbodimides. Carbodimides promote the condensation of an amine and a carboxyl group.

Alternatively, a derivative of gellan gum can be prepared that has free sulfide groups covalently attached to the carbohydrate chain. For instance, if gellan gum is reacted with an aminothiol compound such as 2-mercaptoethylamine and a carbodiimide, the carboxyl group of the gellan and the amine group of the aminothiol compound form an amide bond. A gel-forming polymer having thiol groups has the advantage of having no charge, and the free thiol groups may be used to form reversible gels based on the state of the solution.

In addition to using divalent metal cation or diamine (with or without disulfide) cross-linking agents to modify the properties of the gellan gels of the invention, the properties of these gels can be modified by the incorporation of size-separation property modifying polymers into the gels, as discussed next.

Gellan gum is an anionic polymer due to the presence of carboxylic acid groups in the glucuronic acid residues in the polysaccharide backbone. The negative charge of the carboxyl group requires a counterion, and when an electric field is applied, these cationic counterions (along with waters of hydration) migrate to the negative electrode due to electroosmosis. The result is a net flow of buffer toward the negative electrode. Negatively charged biomolecules such as DNA, which migrate to the positive electrode during electrophoresis, are slowed in their progress as they have to journey against the opposing flow of the buffer. Similarly, the negatively charged glucuronic acids in the gellan attempt to migrate to the positive electrode, thereby destabilizing the gel structure. Addition of certain water soluble polymers to the gellan solution prior to gel formation incorporates the water soluble polymers into the electrophoresis gel. The presence of the water soluble polymer is observed to not only reduce electroosmosis, but also to increase the resolution of lower molecular weight biomolecules. These water soluble polymers, which are referred to herein as size-separation property modifying polymers, are described in Cole et al., "Modification of the Electrokinetic Properties of Reversible Electrophoresis Gels for the Separation and Preparation of DNA", *Applied Biochemistry and Biotechnology*, 82, 57-76, (1999).

A variety of polymers, both linear and branched, can be incorporated into the gellan gum electrophoresis gels to modify the size-separation properties of the gel. Some examples of polymers which can be used include, without limitation:

dextran, Ficoll, amylose, alginates, amylopection, xanthan gum, whelan gum, hydroxyethyl cellulose, methyl cellulose, poly(alkylene oxide) and particularly poly(ethylene oxide), polyvinylpyrrolidone, and polyvinylalchol. Typically, increasing the concentration of the polymer reduces the electroosmotic flow in the gels. It is also observed that higher molecular weight polymers are typically more effective at reducing electroosmotic flow than are lower molecular weight polymers.

The gellan of the present invention may be combined with a buffer solution. Preferred buffer solutions are capable of maintaining the pH of the gellan-based electrophoresis gel within a range of about 5-9 because some biomolecules are susceptible to damage at pH values outside this range. Suitable buffer solutions are selected based, in part, on the type of cross-linking agent used during gel formation. For example, when the cross-linking agent is a diamine, it is desired that the buffer solution maintain the pH of the gel below the pKa of the diamine to ensure that the amino groups are protonated. Examples of buffers suitable for the gellan-based electrophoresis gels of the present invention are shown in the Table below.

TABLE

Buffers Used for Gellan Gum Gel Electrophoresis

| Buffer | Composition | pH |
|---|---|---|
| TB | 0.045 mol/L tris(hydroxymethyl)aminomethane (Tris) and 0.045 mol/L boric acid | 8.5 |
| TA | 0.045 mol/L tris(hydroxymethyl)aminomethane (Tris) and 0.045 mol/L boric acid | 8.3 |
| TG | 0.04 mol/L TRIS and 0.1 mol/L acetic acid | 8.3 |
| BBE | 0.022 mol/L bis (2-hydroxyethyl) imino-tris (hydroxymethyl) methane, 0.045 mol/L boric acid | 6.8 |

During electrophoresis, positively charged ions in the buffer move to the negative electrode, while negatively charged ions move to the positive electrode. Due to electroosmosis of the buffer during electrophoresis, a pH gradient may form across the gel between the positive and negative electrodes. This is problematic because pH variation may cause the diamine cross-linker to become deprotonated, thereby adversely affecting the gel strength. It can also cause heat build-up. Typically, a buffer solution needs to be rapidly recirculated during electrophoresis in order to eliminate this pH gradient. However, a buffer solution with strong buffering capacity is able to maintain the desired pH without recirculation. The present invention provides a buffer composition having strong buffering capacity comprising imidazole and boric acid, which is capable of maintaining the pH within the range of 6.5-8.5. EDTA may optionally be added to the buffer solution. An example of a buffer composition of the present invention is 20-60 mM (e.g., 44 mM) imidazole and 100-300 mM (e.g., 200 mM) boric acid, which is capable of maintaining pH at 6.5-8.5 without being recirculated during electrophoresis. 1-3 mM (e.g., 2 mM) of EDTA may be optionally added to this buffer composition.

The present invention further provides a kit useful in preparing an electrophoresis gel. A kit of the invention includes gellan, preferably in suspension or solution form, a buffer and a cross-linking agent. Both the gellan solution/suspension and the buffer can be present in concentrated form and then diluted to the proper concentration for gel-casting. In one embodiment, each of the kit components is in separate containers. However, the kit may alternatively, or additionally, contain purified gellan in pre-cast form, i.e., the gellan is in combination with, and has been cross-linked by, the cross-linking agent and has been poured into a form that is ready to place directly into an electrophoresis device. When the kit contains gellan only in pre-cast form, the kit may or may not contain cross-linking agent in a separate container. The buffer is the running buffer for the gel electrophoresis, and may optionally be in combination with the gellan so that the gellan is provided in solution or suspension form. Depending on the biomolecules to be resolved, the gellan solution/suspension may optionally contain a size-separation property modifying polymer as described above. In addition, dye may optionally be added to the gellan solution/suspension to help with visualizing the wells for gel loading. Examples of suitable dyes include bromophenol blue, xylene cylanole, and orange G. Likewise, nucleic acid stain, such as ethidium bromide or Syber green may also be added to the gellan solution/suspension, alone or in combination with the dye, depending on the biomolecules to be resolved. The concentration of these materials that may be included in the gellan gel are the same concentrations as are currently used in the art when these materials are utilized in electrophoresis gels made from alternative materials. For example, a concentration of ethidium bromide of about 0.5 mM is suitable in many instances.

In another aspect, the present invention provides a method of performing electrophoresis that includes forming an electrophoresis gel medium by combining ingredients that include (a) a matrix composition comprising gellan solution, nucleic acid at a concentration of less than 10 ppm based on the weight of the gellan, and a size-separation property modifying polymer; (b) a buffer; and (c) a cross-linking agent.

The present invention further provides an electrophoresis apparatus that includes (a) a cross-linked matrix formed by combining gellan solution, cross-linking agent, nucleic acid at a concentration of less than 10 ppm based on the weight of the gellan, buffer, and size-separation property modifying polymer; and (b) an apparatus for exposing said cross-linked matrix to an electric field, including a variety of conventional formats such as flat bed apparatus, vertical slab apparatus, tubes and capillary tubes.

In addition, the present invention provides a method for recovering a biological material, where the method includes (a) adding a mixture that includes a biological material to a cross-linked electrophoresis medium, the medium being formed by a method that includes combining a cross-linking agent and gellan contaminated with less than 10 ppm nucleic acid based on the weight of the gellan; (b) exposing the medium to an electric field to separate in said medium the biological material from other components in the mixture; (c) removing a zone of the medium containing the biological material from the medium; and (d) exposing the removed zone to an agent that reverses the cross-linking of the medium to thereby provide liquefied electrophoresis medium. Optionally, the method further includes a step (e) separating the biological material from the liquefied electrophoresis medium, thereby recovering the biological material; or a step (f) using the solution without removing the polymer.

Electrophoresis gels made from the purified gellan of the present invention afford many desirable properties and advantages over alternative gel matrix compositions. One primary advantage is that the purified gellan of the present invention can be formed into a gel matrix for electrophoresis, where that gel matrix emits less background fluorescence in those instances where nucleic acid is separated on the gel matrix and a fluorescent intercalating agent is used to visualize the bands of resolved nucleic acid. In addition, the gel matrix made from the purified gellan is non-toxic, however it may optionally contain some DNA intercalating agent, e.g., ethidium bromide. However, the present inventors recommend using a non-toxic stain like Syber Green, which actually improves the visibility of the bands. The gellan matrix is very easy to cast, in that one needs only to heat the purified gellan solution to a temperature of 75° C. or greater, add the cross-linker, and then pour the matrix into the electrophoresis mold. In contrast, many agarose-based products require a step of measuring various components, mixing them together, and heating to 100° C., which increases the risk of burning the user and sometimes causes the solution to boil over the top of the flask. Thus, an electrophoresis gel made from the prepared gellan matrix is much easier, safer, and quicker to prepare than a corresponding gel made from, e.g., agarose.

Also, in contrast to many agarose-based products, the gellan gels of the present invention provide better commercial value in that relatively less of the gellan is required to make a gel having the desired consistency for gel electrophoresis. Additionally, a gel matrix made from the purified gellan of the invention affords really sharp bands when linear DNA fragments are separated, and the resolving power of the gel matrix is also very good. An added advantage is that more DNA can be loaded on the gel without sacrificing band sharpness and resolution.

The gellan gels readily set up into a hard matrix upon cooling to about 30° C., and can be re-liquefied by heating to about 95°-100° C., depending upon other gel components that are present. The initial melting of the purified gellan prior to forming the electrophoresis gel matrix, as well as an optional re-heating to re-liquefy the gel matrix in the event it undesirably solidifies, can be readily achieved by simply placing the composition into a microwave oven and bringing to the boiling point.

Alternatively, the product matrix can be returned to a liquefied form upon breaking the cross-linking bonds, where this bond breaking process is initiated under conditions specific to the cross-linker, e.g., using a reducing agent when the cross-linker contains a disulfide bond, or raising the pH when the cross-linker contains protonated amines, or adding a chelating agent when the cross-linker is a divalent metal ion. In effect, this allows the gellan gels of the present invention to be liquefied by breaking the bonds chemically rather than melting the gel at high temperatures, offering significant advantages over existing electrophoresis gels. Currently, almost all DNA is extracted by melting the agarose gels, which are typically "low-melting point agarose" gels that melt at a lower temperature than regular agarose and offer less of a chance for heat damage to occur to the DNA sample. Despite this improvement, heat damage can still occur because most low melting point gels require temperatures of 55° C. to 65° C. in order to actually melt, and the proteins and the DNA components begin to denature at 55° C. In contrast, the gellan gels of the present invention provide a higher quality DNA sample because they are not subjected to temperatures that can damage the DNA. Low-melting point agarose is also problematic because it cools quickly and often solidifies in equipment (e.g., pipettes), often requiring time-consuming recovery procedures or the user to start over again. This is not a problem with the gellan-based gels of the present invention because they remain liquid at room temperature once reversed chemically.

In summary, the gellan-based gels of the present invention are easier to use, save time, and produce a higher quality DNA sample than existing preparative gels. In addition to the foregoing desirable properties and/or advantages of the gellan-based gels of the present invention, it has been observed that persons working with the biomolecules resolved using the gellan-based gels can manipulate those resolved biomolecules when those molecules are still in combination with the gel matrix. Thus, certain reactions can be conducted on the excised resolved biomolecule(s), and it is not necessary to purify the biomolecule from the gellan.

For instance, nucleic acids, such as DNA, are examples of biological material that can be recovered through electrophoresis using gellan-based gel. After separation, bands containing DNA can be excised with a blunt spatula and placed in a microfuge tube. In the case of DNA isolated from gels cast with divalent cation such as $Ca^{2+}$, a concentrated solution of 0.5 M EDTA (pH 8.0) may be added to the gel slice so the final EDTA concentration is about 5 mM. In the case of DNA isolated from gels cast with a diamine (e.g., DAHP), a concentrated solution (pH 8.5) of TRIS may be added to the gel slice so the final concentration is 50 mmol/L TRIS. In the case of DNA isolated from gels cast with cystamine, a concentrated solution of DTT may be added to the gel slice so the final concentration of DTT is about 10 mmol/L. Gentle mixing is typically sufficient to dissolve the gel. The reaction is faster if the gel slice and DTT are incubated at 45 to 55° C. Alternatively, DNA can be gently and efficiently recovered from gellan gels that are cross-linked cystamine by means of a gellan-digesting enzyme, gellanase (U.S. Pat. No. 5,342,773).

DNA isolated from gellan electrophoresis gel can be readily cut by a variety of restriction enzymes (e.g., Eco RI, Hind III, and Bam H1) in the presence of gellan gum. The restriction enzyme (ca. 10 units) can be added directly to the dissolved gel band and the solution mixed. A 10× restriction buffer should then be added, and the tube contents mixed and incubated at 37° C. for 2-4 hrs. The restriction fragments can be analyzed by electrophoresis.

The activity of DNA ligase is not significantly inhibited by gellan gum as determined by analysis of the restriction fragments using agarose gel electrophoresis. Ligase (1 unit) can be added directly to a mixture of the restriction fragments resulting from the restriction digestion as mentioned above. 5× ligase buffer may then be added, the tube contents mixed together and incubated at 37° C. for 2-4 hrs. Successful ligation of the DNA restriction fragments is indicated by the formation of higher molecular weight products when analyzed by gel electrophoresis.

DNA isolated from gellan gum electrophoresis gels can be used in direct transformation of *E. coli*. The dissolved gel solution (e.g., 0.05 mL) containing isolated DNA may be placed on ice and competent cells (e.g., 0.05 mL) are added to a final volume of ca. 0.1 mL. Transformation can be done according to the supplier's instructions. Typically, this consists of incubation on ice for 30 min, heat shock at 37° C. for 45 seconds, cooling on ice for 2 min, and addition of 0.95 mL of LB media. The tubes are then incubated at 37° C. with shaking (225 rpm) for about 1 hr. The cells are diluted and plated out on LB plates containing antibiotics. Colonies are counted the next day after incubation at 37° C.

DNA isolated from gellan gum electrophoresis gels followed by ligation to other DNA transforms *E. coli* competent cells with about the same frequency as low melting point agarose. To remove gellan from a dissolved gellan gel sample containing isolated target biomolecule, such as DNA, a solution of $CaCl_2$ may be added to the sample to a concentration of ca. 5 mmol/L or greater. The solution is mixed and the cross-linked gellan gum can be removed by centrifugation, for example at 12,000×g for 15 min, or by filtration. The gellan gum is collapsed into a compact pellet (centrifugation) or retained on a filter (filtration) leaving the target molecule in solution. Alternatively, the gellan slice can also be soaked for a short while in a diffusion buffer [0.5M Ammonium acetate, 1 mM EDTA] at 37° C. The gel is then centrifuged as above. The solution on top is then brought to 2.5 M ammonium acetate and the DNA precipitated with 2½ volumes of ETOH. This diffusion buffer may be a component in kit of the present invention.

Proteins can also be separated by electrophoresis using gellan gel. and positively charged proteins move towards the negative electrode. Adding size-separation property modifying polymers to the gel can reduce the electroosmotic flow contributed by the charge on the gellan matrix. They also aid in separation.

The following examples are supplied so as to provide those of ordinary skill in the art with a complete disclosure and description of how to make and use the subject invention, and are not intended to limit the scope of what is regarded as the invention.

EXAMPLES

Example 1

Gellan Purification

A solution of 35 mM sodium azide and 5 µ/ml DNase 1 in deionized water was made, to which commercial gellan [Kelcogel Fine (KGF), purchased from CPKELCO] was added to make a 1.75 wt % gellan suspension. This is 10 times more concentrated than the final gellan solution ready for gel-casting. The mixture was shaken at 37° C. At any point, 10 ml of the suspension could be extracted and diluted with 1 ml of buffer. 0.5 mM ethidium bromide could be added before the mixture is placed on a UV transilluminator to monitor the loss of fluorescence, which indicates the degree of nucleic acid degradation. Typically, there was no detectable nucleic acid contaminant after the suspension had been shaken for 20 hours. The mixture was then heated to 75° C. for 4 hrs to deactivate the DNase 1. The resulted gellan solution can be used directly or diluted for casting electrophoresis gel. The purified gellan may be isolated from the solution, however, it may also be retained in the solution and an electrophoresis slab formed from the solution.

Example 2

Buffer Preparation

A mixture of 0.44 M imidazole, 2.0 M boric acid and 0.02 M EDTA in deionized water was stirred at room temperature for 2-3 hrs until all the components were dissolved. Optionally, 5 µg/ml ethidium bromide could be added. The resulting buffer is 10 times more concentrated than will typically be used in gel electrophoresis. It should be diluted for use in gel-casting and performing the electrophoresis.

Example 3

Size-seperation Modifying Polymer Solution Preparation

While the size-separation modifying polymers are all water-soluble, somewhat different procedures may be followed in order to dissolve them in solution forming polymer solutions may require different care depending on their molecular weight (MW).

For example, poly(ethyleneoxide) (MW=4,000,000) was added to deionized water to make a 0.5 wt % mixture. It was necessary to agitate the mixture for about 24 hours to ensure that all the polymer particles had completely dissolved.

Poly(Poly(ethyleneoxide) (MW=100,000) was added to deionized water to make a 2 wt % mixture. The mixture was heated to boiling to dissolve all the polymer particles.

Example 4

General Procedure for Gel Formation and Electrophoresis

The concentrated gellan solution prepared according to Example 1 was mixed with the buffer solution of Example 2 and diluted with deionized water so the final concentrations are: gellan at 0.17 wt %, imidazole at 44 mM and boric acid at 200 mM. Optionally the solution could be further combined with the size-separation property modifying polymer solution, where the final concentration of the polymer can be adjusted depending upon the biomolecules to be resolved. The solution was then heated to a temperature in excess of 75° C. At this point, cystamine was added so that its final concentration was between 2.5 to 10 mM. Optionally, nucleic acid stain may also be added. The solution was then poured into the gel tray and allowed to solidify. A comb was then suspended in the gel to form the sample wells. A flat bed submarine gel electrophoresis apparatus was used. The electrode buffer chambers were filled with the electrophoresis buffer (44 mM imidazole and 200 mM boric acid). The samples of biomolecules were diluted with a buffer solution containing a trace of bromophenol blue, so the final concentration of the samples was approximately 2 wt %. The samples were loaded into the wells. 2.5 mM cross-linker was added to the anode chamber and the electric field was applied. Typically, the gel can be run at 7 volts/cm.

Example 5

Formation of Gellan Electrophoresis Gels Using Cystamine and Gel Liquefaction

Strong stable gels were formed when cystamine (5 mM) in imidazole/boric acid buffer (44 mM imidazole, 200 mM boric acid, pH=6.8) was added to gellan suspension to form a gellan electrophoresis gel (0.1 wt %). A solution of dithiothreitol (0.01 mol/L) was added to the gellan electrophoresis gel (0.01%) whereupon the gel converted back to solution.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A purified gellan composition containing nucleic acid at a concentration of less than 10 ppm based on the weight of gellan prepared by combining DNase and an unpurified gellan composition contaminated with nucleic acid to make a mixture wherein said mixture is maintained under conditions such that DNase degrades at least some of the nucleic acid, thereby resulting in the purified gellan composition.

2. The purified gellan composition of claim 1 wherein the concentration of nucleic acid in the unpurified gellan composition is more than 100 ppm based on the weight of gellan.

3. The purified gellan composition of claim 1 wherein the purified gellan composition contains less than 50% of the nucleic acid in the unpurified gellan composition.

4. The purified gellan composition of claim 1 wherein said mixture further comprises a DNase activating agent.

5. The purified gellan composition of claim 4 wherein the DNase activating agent is sodium azide.

6. The purified gellan composition of claim 1 wherein said mixture is maintained at 30-45° C. for at least 1 hour.

7. The purified gellan composition of claim 1 wherein in preparing the purified gellan composition, nucleic acid degradation is monitored.

8. The purified gellan composition of claim 1 wherein after the mixture is maintained under conditions such that DNase degrades at least some of the nucleic acid, the DNase is deactivated.

9. The purified gellan composition of claim 8 wherein the DNase is heat deactivated by heating the DNase to an inactivating temperature in excess of 50° C.

10. The purified gellan composition of claim 1 wherein the DNase is DNase 1.

11. The purified gellan composition of claim 1 wherein in preparing the purified gellan composition, boric acid is added to the unpurified gellan composition or the purified gellan composition.

12. The purified gellan composition of claim 1 wherein in preparing the purified gellan composition, imidazole is added to the unpurified gellan composition or the purified gellan composition.

13. The purified gellan composition of claim 1 wherein in preparing the purified gellan composition, a size-separation property modifying polymer is added to the unpurified gellan composition or the purified gellan composition.

14. The purified gellan composition of claim 13 wherein the size-separation property modifying polymer is poly (ethylene oxide).

15. A gellan composition comprising water and gellan, the composition containing either no nucleic acid or nucleic acid at a concentration of less than 10 ppm based on the weight of the gellan.

16. The gellan composition of claim 15 that contains either no nucleic acid or nucleic acid at a concentration of less than 5 ppm based on the weight of the gellan.

17. The gellan composition of claim 15 that contains either no nucleic acid or nucleic acid at a concentration of less than 1 ppm based on the weight of the gellan.

18. A gellan composition, comprising:
    (a) gellan; and
    (b) either no nucleic acid or nucleic acid at a concentration of less than 10 ppm nucleic acid, based on the weight of gellan.

19. The composition of claim 18 further comprising a size-separation property modifying polymer.

20. The composition of claim 19 wherein the size-separation property modifying polymer is poly(ethylene oxide).

21. The composition of claim 18 further comprising a buffer for maintaining said composition at a pH of 5-9.

22. The composition of claim 21 wherein the buffer comprises imidazole or a salt thereof and boric acid or a salt thereof.

23. The composition of claim 18 further comprising EDTA or a salt thereof.

24. The composition of claim 18 further comprising a size-separation property modifying polymer, imidazole or a salt thereof, boric acid or a salt thereof, and EDTA or a salt thereof.

25. The composition of claim 18 further comprising a cross-linking agent.

26. The composition of claim 25 wherein the cross-linking agent is cystamine.

27. A kit comprising:
    (a) a matrix composition comprising gellan and nucleic acid at a concentration of less than 10 ppm based on the weight of the gellan;
    (b) buffer; and
    (c) cross linking agent.

28. The kit of claim 27 wherein the nucleic acid is present in the matrix composition at a concentration of less than 5 ppm based on the weight of the gellan.

29. The kit of claim 27 wherein the matrix composition further comprises a size-separation property modifying polymer.

30. The kit of claim 29 wherein the size-separation property modifying polymer is poly(ethylene oxide).

31. The kit of claim 27 further comprising a size-separation property modifying polymer.

32. The kit of claim 31 wherein the size-separation property modifying polymer is poly(alkylene oxide).

33. The kit of claim 27 wherein the matrix composition further comprises boric acid or a salt thereof.

34. The kit of claim 27 wherein the matrix composition further comprises imidazole or a salt thereof.

35. The kit of claim 27 wherein the matrix composition has a pH between 6.5 and 8.5.

36. The kit of claim 27 wherein the matrix composition further comprises a DNA stain.

37. The kit of claim 27 wherein the buffer comprises imidazole or a salt thereof.

38. The kit of claim 27 wherein the buffer comprises boric acid or a salt thereof.

39. The kit of claim 27 wherein the buffer comprises imidazole or a salt thereof, and boric acid or a salt thereof.

40. The kit of claim 27 wherein the cross linking agent is cystamine.

* * * * *